(12) United States Patent
Duprez et al.

(10) Patent No.: US 11,529,457 B2
(45) Date of Patent: Dec. 20, 2022

(54) MEDICAL DEVICE HAVING A DETACHABLE COVER ELEMENT

(71) Applicant: Fresenius Vial SAS, Brézins (FR)

(72) Inventors: Remi Duprez, Coublevie (FR); Damien Archat, Grénoble (FR); Mathieu Paoli, La Murette (FR); Abdel-Nasser Jhuboo, Saint Simeon de Bressieux (FR); Thibault Cretinon, Tassin la Demi Lune (FR)

(73) Assignee: Fresenius Vial SAS, Brézins (FR)

( * ) Notice: Subject to any disclaimer, the term of this patent is extended or adjusted under 35 U.S.C. 154(b) by 171 days.

(21) Appl. No.: 16/646,949

(22) PCT Filed: Aug. 31, 2018

(86) PCT No.: PCT/EP2018/073419
§ 371 (c)(1),
(2) Date: Mar. 12, 2020

(87) PCT Pub. No.: WO2019/057467
PCT Pub. Date: Mar. 28, 2019

(65) Prior Publication Data
US 2020/0268963 A1    Aug. 27, 2020

(30) Foreign Application Priority Data
Sep. 20, 2017   (EP) .................... 17306226

(51) Int. Cl.
*A61M 5/145*    (2006.01)
*A61M 5/142*    (2006.01)
(Continued)

(52) U.S. Cl.
CPC .......... *A61M 5/142* (2013.01); *A61M 5/1456* (2013.01); *D06F 39/14* (2013.01); *A61M 2205/14* (2013.01); *D06F 34/20* (2020.02)

(58) Field of Classification Search
CPC .......... A61M 25/02; A61M 2025/0233; A61M 2025/028; A61M 2025/0286;
(Continued)

(56) References Cited

U.S. PATENT DOCUMENTS 4,084,214 A    4/1978 Eppich
5,364,364 A *  11/1994 Kasvikis ........... A61M 5/14228
                                                    137/556

(Continued)

FOREIGN PATENT DOCUMENTS

DE           3242351 A1    5/1984
DE       10 2012 016938    9/2013
(Continued)

OTHER PUBLICATIONS

International Search Report and Written Opinion, counterpart International Appl. No. PCT/EP2018/073419 (dated Sep. 28, 2018) (13 pages).

(Continued)

*Primary Examiner* — Laura A Bouchelle
(74) *Attorney, Agent, or Firm* — Cook Alex Ltd.

(57) ABSTRACT

Medical device having a detachable cover element A medical device (1) for administering a medical solution to a patient comprises a housing (10), a receptacle (12) for receiving a pumping apparatus (3) for administering the medical solution to the patient, and a cover element (2) for covering the receptacle (12). The cover element (2), in a connected state, is pivotably connected to the housing (10) about a pivot axis (P) by means of a hinge connection, the hinge connection being releasable for detaching the cover element (2) from the housing (10). In this way a medical device is provided which may have an increased adjustability for use in different environments in a healthcare environment.

14 Claims, 8 Drawing Sheets

(51) Int. Cl.
*D06F 39/14* (2006.01)
*D06F 34/20* (2020.01)

(58) Field of Classification Search
CPC ....... A61M 2025/0293; E05D 11/1007; E05D 11/018; E05D 11/0027; E05D 2011/0036; E05D 2011/0045; E05D 7/1011; E05D 5/12; E05D 3/00; E05D 3/02
See application file for complete search history.

(56) References Cited

U.S. PATENT DOCUMENTS

| | | | | |
|---|---|---|---|---|
| 5,482,446 | A | * | 1/1996 | Williamson .......... A61M 5/142 |
| | | | | 417/234 |
| 5,769,261 | A | | 6/1998 | Gaffney et al. |
| 5,928,177 | A | * | 7/1999 | Brugger .............. F04B 43/1284 |
| | | | | 604/6.11 |
| 8,118,778 | B2 | * | 2/2012 | Haylor ................ A61M 5/1413 |
| | | | | 604/131 |
| 2010/0063448 | A1 | | 3/2010 | Kragh et al. |
| 2010/0146734 | A1 | * | 6/2010 | Munson ................. E05D 5/121 |
| | | | | 16/334 |
| 2013/0007986 | A1 | * | 1/2013 | Flaman .................... E05D 3/02 |
| | | | | 16/387 |
| 2016/0324725 | A1 | | 11/2016 | Horn |
| 2017/0018155 | A1 | | 1/2017 | Ricks et al. |

FOREIGN PATENT DOCUMENTS

| | | |
|---|---|---|
| EP | 1223281 A2 | 7/2002 |
| WO | WO2006/008465 A1 | 1/2006 |
| WO | WO2013/046611 A1 | 4/2013 |

OTHER PUBLICATIONS

Search Report, counterpart Chinese App. No. 201880043596 (dated Sep. 29, 2021) (2 pages).

* cited by examiner

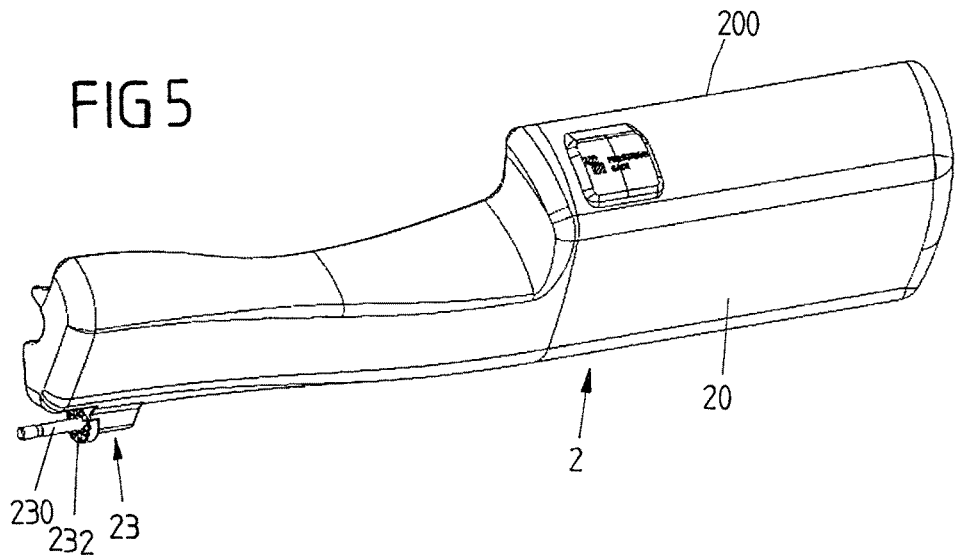
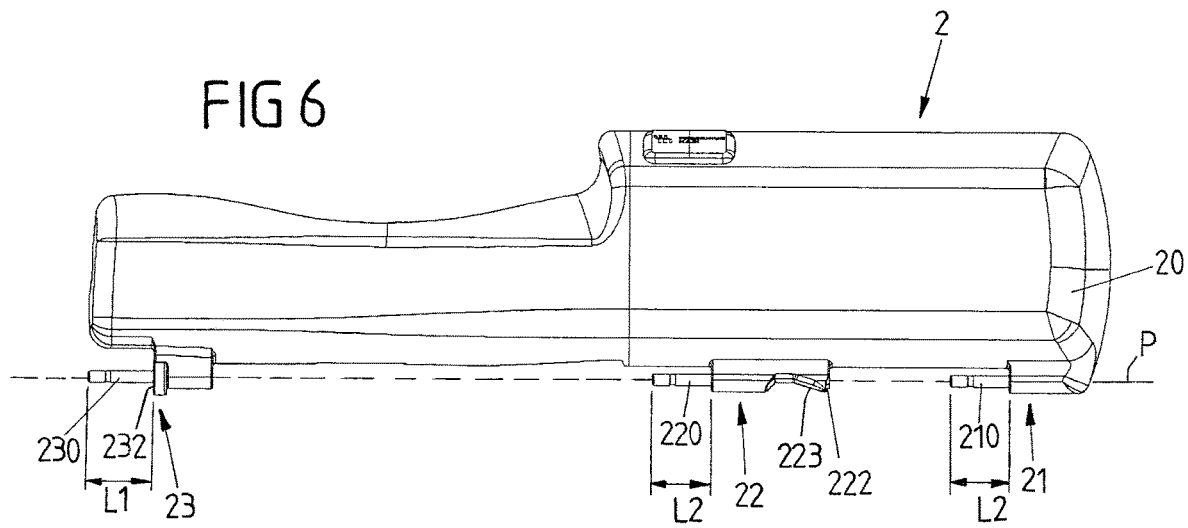
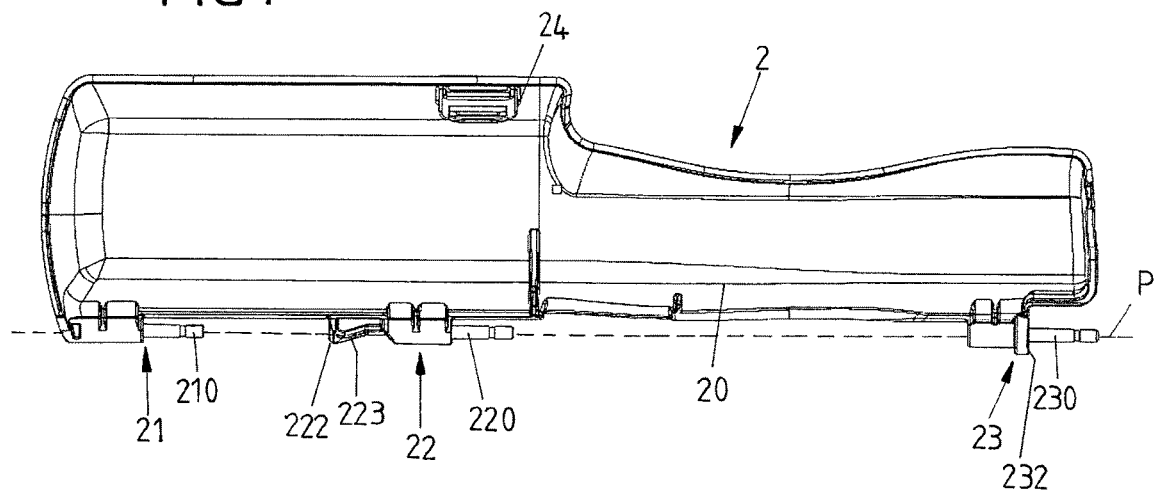

MEDICAL DEVICE HAVING A DETACHABLE COVER ELEMENT

The present application is a U.S. National Stage of PCT International Patent Application No. PCT/EP2018/073419, filed Aug. 31, 2018, which claims priority to EP Application No. 17306226, filed Sep. 20, 2017, both of which are hereby incorporated herein by reference.

The invention relates to a medical device for administering a medical solution to a patient according to the preamble of claim 1.

A medical device of this kind comprises a housing, a receptacle for receiving a pumping apparatus for administering the medical solution to the patient, and a cover element for covering the receptacle.

A medical device of this kind may for example be constituted as a syringe infusion pump. In this case a syringe is placed, with its cylindrical barrel, in a receptacle of the device and is brought into operative connection with a pumping mechanism of the medical device such that, during operation, the pumping mechanism acts onto a piston of the syringe in order to deliver a medical fluid from the barrel via a delivery line connected to the barrel towards the patient.

The medical device, in another embodiment, may also be constituted as a volumetric (peristaltic) infusion pump, in which case a pumping apparatus in the shape of an infusion line having for example a pumping module comprising a membrane may be received in a corresponding receptacle of the device. The infusion pump comprises a pumping mechanism for acting onto the membrane of the pumping module such that a medical fluid may be delivered towards the patient through the infusion line in a peristaltic fashion.

Conventional infusion devices comprise a cover element which is pivotably connected to the housing and can be moved in between a closed position, in which the receptacle is covered towards the outside, and an opened position, in which access to the receptacle is granted such that a pumping apparatus, for example a syringe, may be placed within the receptacle or may be taken out of the receptacle.

A cover element of this kind serves to protect the receptacle and, in case of a syringe pump, a fluid container placed within the receptacle against misuse and theft. This is of particular importance in areas of for example a healthcare environment which are accessible by the public, potentially without attention by healthcare personnel, as it may be the case for example in a general ward of a hospital. In such environments the cover element may be closed and locked during an infusion operation such that unauthorized parties may not gain access to the receptacle and a fluid container placed therein.

In other environments, however, for example in an operating room in a hospital, the cover element may not be necessary and may even pose a hindrance for a user, for example a nurse, if for example during an ongoing operation a fluid container must quickly be replaced.

It is an object of the instant invention to provide a medical device which may have an increased adjustability for use in different environments in a healthcare environment.

This object is achieved by means of a medical device comprising the features of claim 1.

Accordingly, the cover element, in a connected state, is movably connected to the housing, the connection being releasable for detaching the cover element from the housing.

In particular, the cover element, in the connected state, may be pivotably connected to the housing about a pivot axis by means of a hinge connection, the hinge connection being releasable for detaching the cover element from the housing.

The cover element hence is releasably connectable to the medical device. If the cover element is (mechanically) connected to the medical device, it can be moved (e.g., pivoted) with respect to the housing of the medical device in between an opened position and a closed position, wherein in the closed position the cover element covers the receptacle and hence may protect the receptacle against unauthorized access from the outside. In the opened position, in contrast, the receptacle is uncovered such that a pumping apparatus (for example a syringe containing a medical fluid) may be placed in the receptacle or may be removed from the receptacle in order to for example replace it by another pumping apparatus.

By releasing the connection the cover element may be separated from the housing such that the cover element is detached from the housing. The cover element may hence be removed from the housing, wherein operation of the medical device may be possible even without the cover element, such that the medical device may be operated for carrying out an infusion operation without its cover element. In such situations and scenarios in which the cover element poses a hindrance, the cover element hence may be removed, and the medical device may be operated without the cover element.

In other situations, in contrast, the cover element may be connected to the housing and closed for carrying out an infusion operation such that the receptacle is protected against unauthorized access from the outside.

A medical device of this kind may for example be constituted by a syringe infusion pump, in which case the pumping apparatus is formed by a syringe to be placed in the receptacle of the housing. During operation, a pusher device of the medical device acts onto a piston of the syringe in order to deliver a medical fluid from a barrel of the syringe via a delivery line towards a patient.

In another embodiment, the medical device may be constituted by a volumetric (peristaltic) infusion device, in which case the pumping apparatus may for example be formed by an infusion line having for example a pumping module to be received within the receptacle of the medical device such that a pumping mechanism of the medical device may act onto the pumping module, for example a membrane of the pumping module, for delivering a medical fluid from a fluid container connected to the infusion line towards a patient.

The hinge connection may be formed by one or multiple hinge devices which are designed to pivotably connect the cover element to the housing. Such hinge devices each may comprise a hinge pin arranged on the cover element or the housing, the hinge pin forming a pivotable connection by engaging in an associated pin receptacle arranged on the other element (if the hinge pins are arranged on the cover element, the pin receptacles for example are arranged on the housing and vice versa). The hinge pins extend longitudinally along the pivot axis and hence, by their engagement in the pin receptacles, provide for a pivotable connection in between the cover element and the housing.

For establishing the hinge connection, the hinge pins of the hinge devices may for example be inserted into the associated pin receptacles in an insertion direction directed along the pivot axis. For establishing the hinge connection, hence, the cover element is placed on the housing such that the hinge pins engage with the pin receptacles in order to form the pivotal connection in between the cover element and the housing.

Herein, in one embodiment a first hinge device (of at least two hinge devices) comprises a first hinge pin having a first length, and a second hinge device (of the at least two hinge devices) comprises a second hinge pin having a second length, wherein the first length is larger than the second length. The hinge pins of the hinge devices hence have different lengths, which may help to ease the positioning of the cover element on the housing in order to establish the connection in between the cover element and the housing.

In particular, the first hinge pin and the second hinge pin may be configured such that, when connecting the cover element to the housing, the first hinge pin of the first hinge device comes into engagement with an associated first pin receptacle prior to the second hinge pin of the second hinge device coming into engagement with an associated second pin receptacle. Thus, when placing the cover element on the housing, at first the hinge pin of the first hinge device engages with its associated pin receptacle, upon which also the hinge pin of the second hinge device comes into engagement with its associated pin receptacle. The engagement of the hinge pins with the associated pin receptacles hence takes place in a consecutive fashion, such that not all hinge pins have to be brought into engagement with their associated pin receptacles at the same time.

In one embodiment, the medical device comprises a blocking device constituted to block, in the connected state of the cover element, a lateral movement of the cover element with respect to the housing. In particular, the blocking device may serve to block the cover element with respect to the housing such that the hinge pins of the hinge devices may not move out of engagement with the associated pin receptacles. The hinge pins hence are held within the pin receptacles, such that the pivotal connection of the cover element to the housing is secured against an involuntary release.

The blocking device, in one embodiment, comprises a blocking pin arranged on one of the housing and the cover element, serving to interact with a blocking element arranged on the other of the housing and the cover element. The blocking pin may in particular be movable and displaceable along a direction transverse to the pivot axis and may be pretensioned towards a position in which it is constituted to block a movement of the cover element with respect to the housing. When placing the cover element on the housing by inserting the hinge pins of the hinge devices into their associated pin receptacles, the blocking pin is displaced (against its pretensioning force, for example exerted by a spring element acting onto the blocking pin) from a normal rest position such that the hinge pins may be brought into engagement with the associated pin receptacles for connecting the cover element to the housing. Once the hinge pins have reached their engagement position, the blocking pin snaps back into its normal rest position (due to the pretensioning force) and in this way blocks an opposite movement of the hinge pins with respect to the pin receptacles.

To ease the connection of the cover element to the housing and/or to allow for an easy disconnection of the cover element from the housing, the blocking pin and/or the blocking element may each comprise a run-up slope causing the blocking pin to be deflected when connecting the cover element to the housing and/or when the cover element shall be released from the housing. Both the establishment of the connection of the cover element to the housing and the release of the connection of the cover element from the housing hence may take place by laterally moving the cover element with respect to the housing along the pivot axis, causing a deflection of the blocking pin by interaction with the blocking element, wherein the force to be applied may depend on the steepness of the run-up slope of the blocking pin and/or the blocking element. In particular, run-up slopes of the blocking pin and the blocking element may be designed such that less force is required for establishing the connection than for releasing the connection.

In one embodiment, the medical device comprises a sensor device for detecting whether a hinge pin is received in an associated pin receptacle. The sensor device may for example comprise a lever movably placed within the pin receptacle. If the hinge pin associated with the pin receptacle is inserted into the pin receptacle it acts onto the lever and hence deflects the lever such that, by determining the lever position, it can be detected whether engagement of the hinge pin with the pin receptacle has correctly been established or not.

In a further embodiment, at least one of the hinge devices may comprise a damping element designed to dampen a pivoting movement of the cover element with respect to the housing. The damping element may for example have the shape of a cylindrical bushing such that upon insertion of the hinge pin into the associated pin receptacle the damping element, for example placed within the pin receptacle, is brought into operative connection with the hinge pin such that a pivoting movement of the hinge pin within the pin receptacle is dampened by the damping element, hence slowing down a rotational movement of the cover element with respect to the housing.

The damping element may for example provide for a friction when moving the cover element with respect to the housing. Alternatively, the damping element may be formed by a fluid damper, for example having a stationary part fixed to the housing and a rotatable part fixable to the cover element, such that the rotatable part is rotated with respect to the stationary part when rotating the cover element. The stationary part may for example enclose a chamber filled with a damping fluid such that by rotating the rotatable part within the chamber defined by the stationary part it is acted onto the damping fluid which in this way is caused to flow past the rotatable part and hence dampens the movement of the rotatable part with respect to the stationary part in a predefined manner, depending for example on the viscosity of the damping fluid.

In one embodiment, the cover element comprises a lock element for locking the cover element with the housing when the cover element is connected to the housing and is closed for covering the receptacle. A lock (which for example is actuatable by a suitable key) may for example be placed on the housing, the lock being preferably biased towards the locked position such that the lock automatically assumes the locked position if not actuated. Upon closing the cover element the lock element of the cover element comes into engagement with a suitable locking mechanism of the lock such that the cover element is locked with respect to the housing and cannot be opened without unlocking the lock, for example by using a suitable key.

A locking sensor may interact with the lock in order to detect whether the lock element engages with the lock. In this way it can be detected whether the cover element is in its closed position or not.

In one embodiment, the cover element comprises a cover body formed from a transparent material. The cover element hence covers the receptacle against access from the outside, but allows for a visual inspection of a pumping apparatus placed within the receptacle.

In the closed position the cover element may abut the housing with a circumferential edge, wherein the abutment may be such that the cover element does not, at its edge, protrude from the housing, but with its edge is (at least partially) received within the housing. In this way the cover element can be designed such that it may not be tampered with the cover element using an external tool for opening the cover element.

In another embodiment the medical device comprises a control device for controlling the operation of the medical device, in particular its pumping operation. In this regard, the control device may be constituted to evaluate a connection state of the cover element and a closing state of the cover element. Dependent on the evaluation, then, the control device may control the operation of medical device.

In particular, the control device may, also dependent on the type of medication to be administered, enable an administration operation without the cover element connected to the housing of the medical device. The medical device hence may be operated without the cover element. This may be allowed only for certain types of medication, whereas for other types of medication a connection of the cover element (and a closing of the cover element) may be mandatory.

Further, the control device may be constituted to enable an administration operation when the cover element is connected to the housing of the medical device, but only if the cover element is in its closed position. If the cover element is present, it hence must be closed in order to allow for an infusion operation.

The idea of the invention shall subsequently be described in more detail with reference to the embodiments shown in the figures. Herein:

FIG. 5 shows a separate view of the cover element;

FIG. 6 shows a front view of the cover element;

FIG. 7 shows a back view of the cover element;

Figure 1:
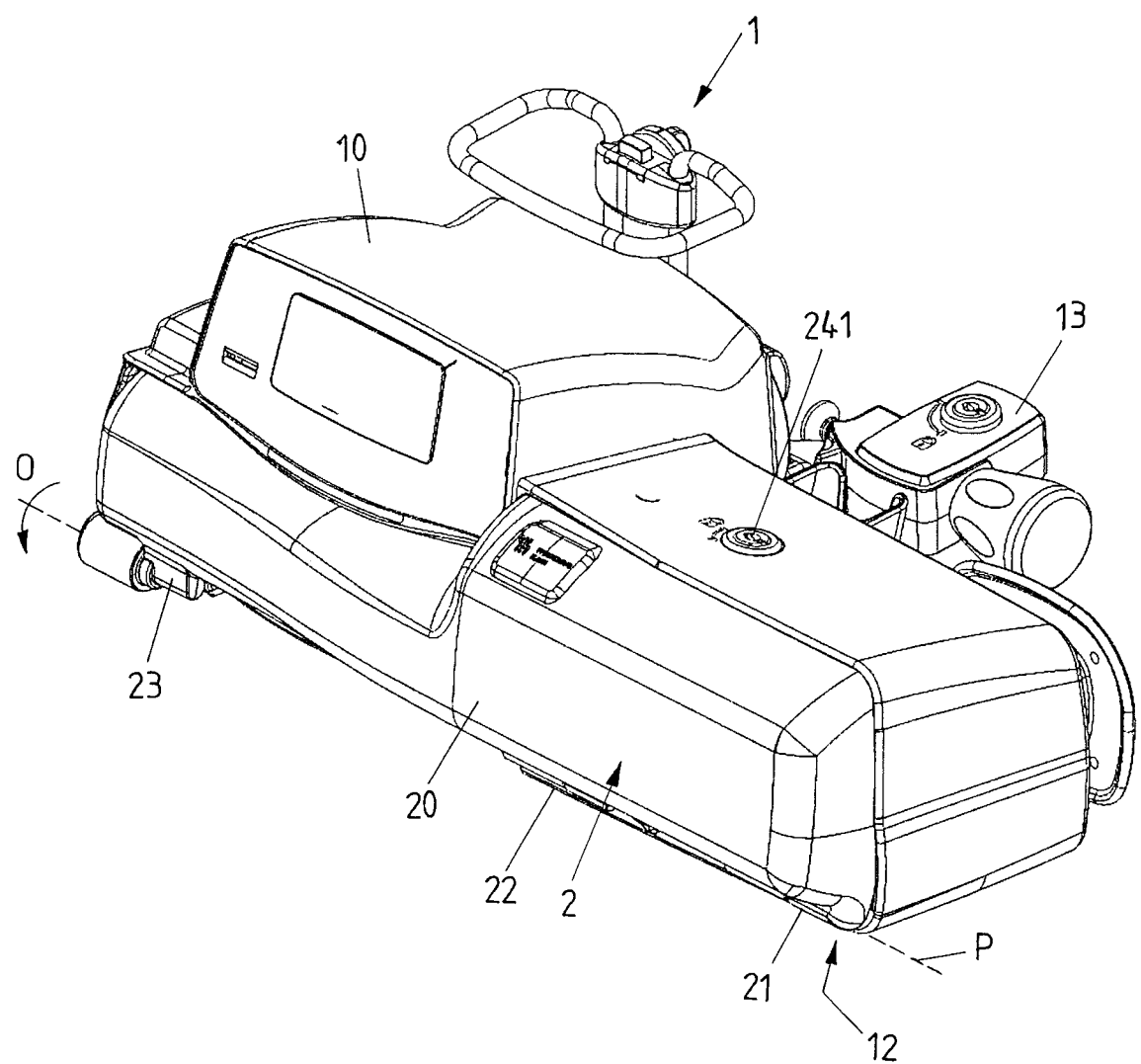
FIG. 1 shows a view of a medical device in the shape of a syringe infusion pump.
Figure 2:
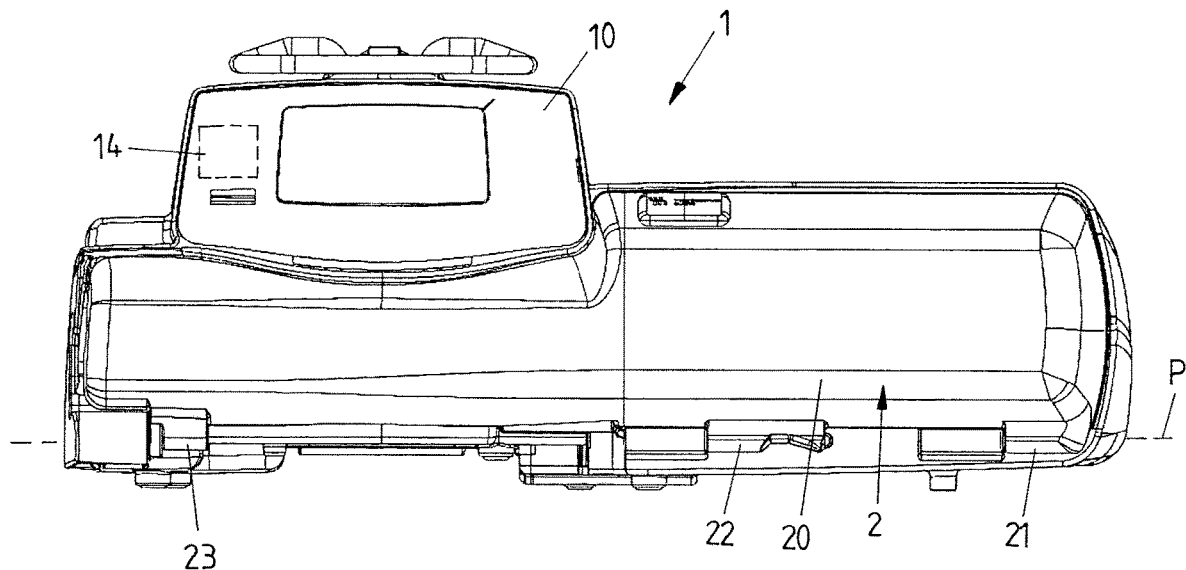
FIG. 2 shows a front view of the medical device.
Figure 3:
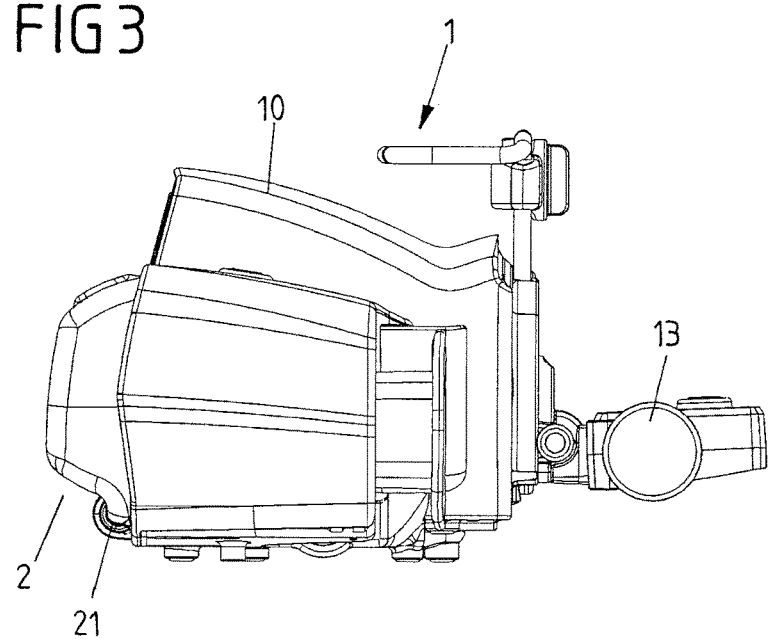
FIG. 3 shows a side view of the medical device.

FIGS. 1 to 3 show an embodiment of a medical device 1 in the shape of a syringe infusion pump having a housing 10 which, by means of a fixation device 13 in the shape of a clamp, can be fixed for example to a stand or the like for placing it at a bedside of a patient or in an operating room in a hospital.

Figure 13:
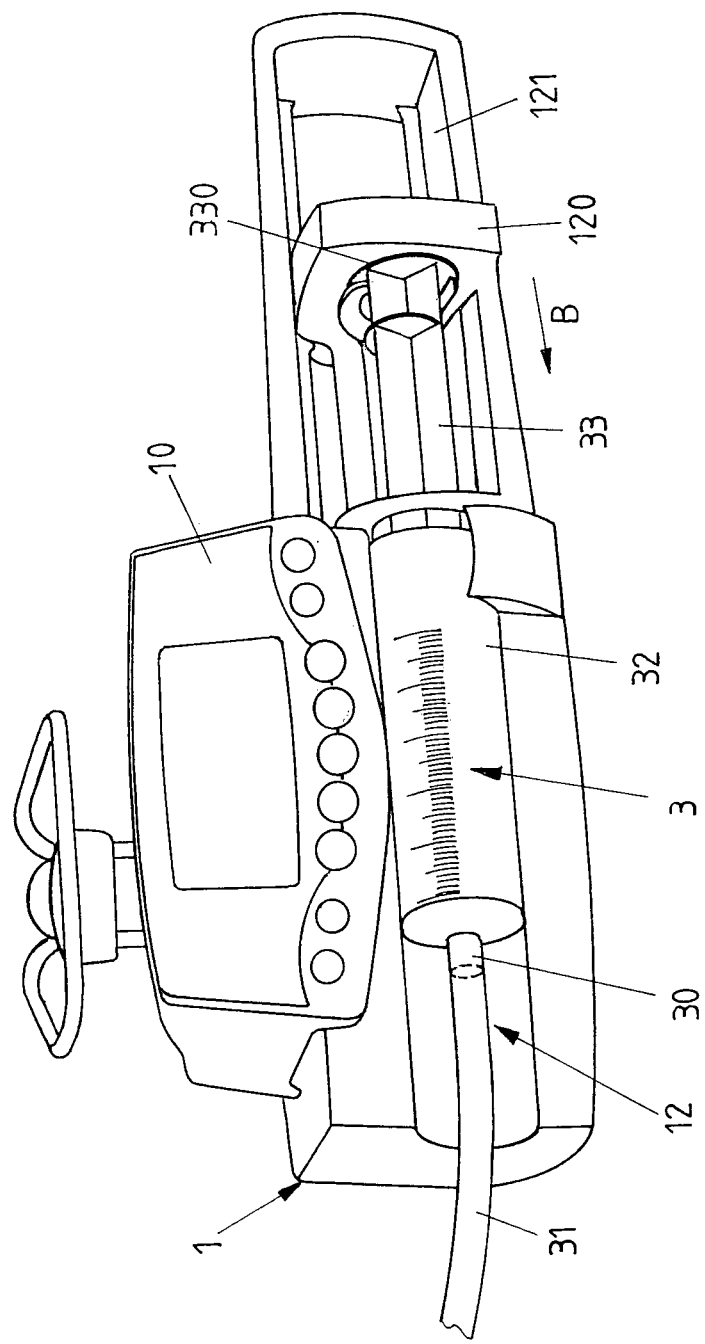
FIG. 13 shows a view of a medical device in the shape of a syringe infusion device.

The medical device 1 serves to administer a medical fluid, such as a medication or a nutritional solution for the enteral feeding, to a patient. For this, the housing 10 forms a receptacle 12, as it is visible for example in FIG. 13, which is configured to receive a pumping apparatus in the shape of a syringe 3 having a cylindrical barrel 32 and a piston 33 movable within the barrel 32. The syringe 3 can be fixed in the receptacle 12 by means of a clamping device 122 such that the cylindrical barrel 32 is held stationary within the receptacle 12. The piston 33, by means of a piston head 330, can be brought into operative connection with a pusher device 120 movable with respect to the housing 10 along a guide track 121 by means of an electromechanical drive mechanism of the medical device 1, such that the piston 33 can be moved by means of the pusher device 120 in an actuation direction B to deliver a medical fluid from the cylindrical barrel 32 via a delivery line 31 connected at a connector 30 to the cylindrical barrel 32 towards a patient.

The medical device 1, in the embodiment of FIGS. 1 to 3, comprises a cover element 2 having a cover body 20 formed from a transparent material and being pivotable with respect to the housing 10 about a pivot axis P. The cover element 2 is, in a connected state as shown in FIGS. 1 to 3, connected to the housing 3 by means of three hinge devices 21, 22, 23 forming a hinge connection which allows to pivot the cover element 2 from a closed position in an opening direction O with respect to the housing 10 in order to open the cover element 2 and to allow access to the receptacle 12 formed on the housing 10, and vice versa to close the cover element 2 in order to cover the receptacle 12 in a closed position.

Figure 4:
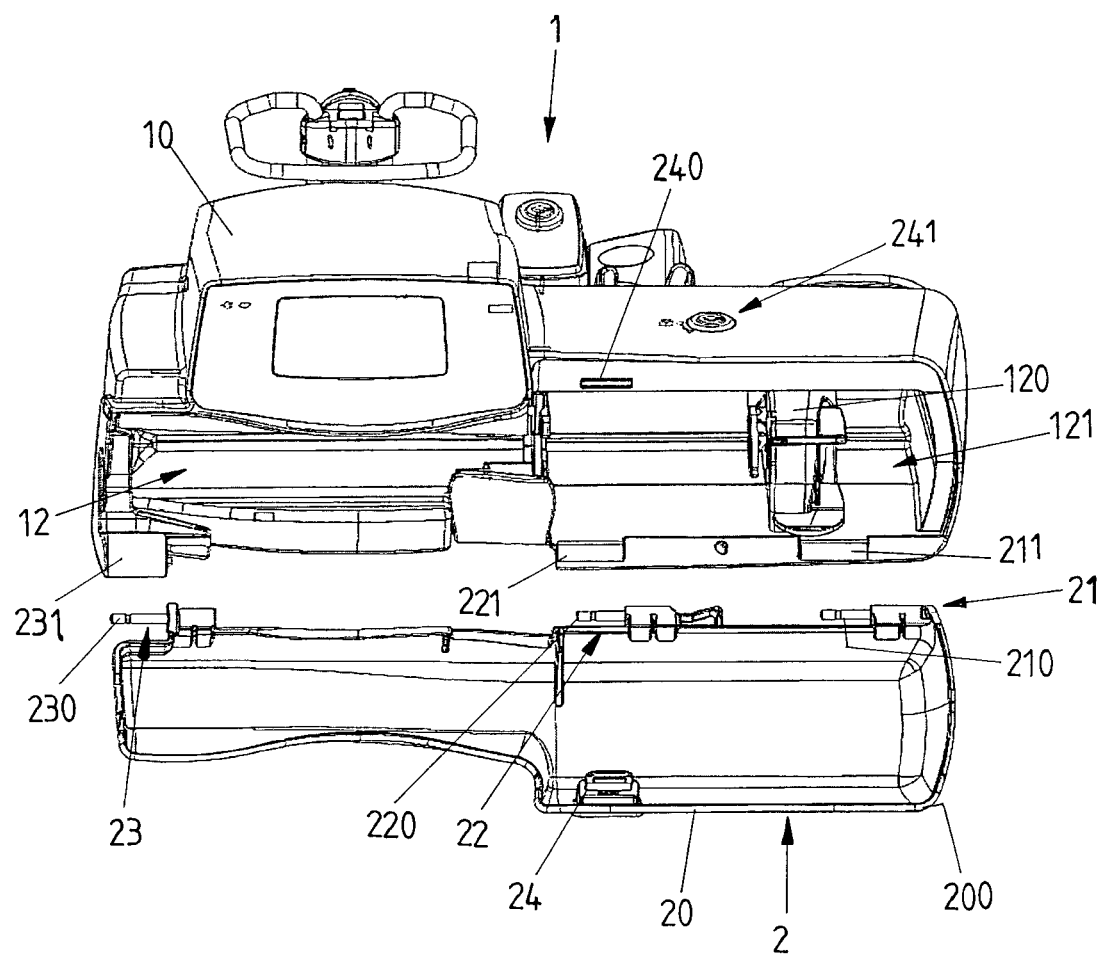
FIG. 4 shows another view of the medical device, with a detached cover element.
Figure 8:
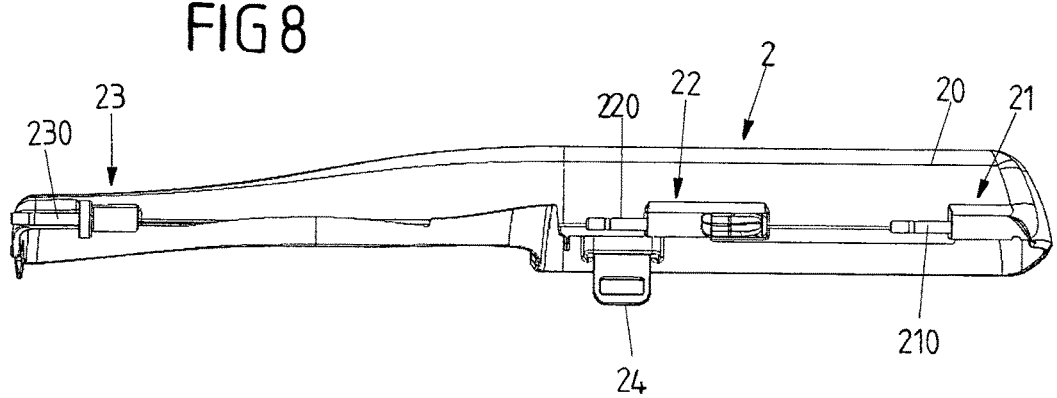
FIG. 8 shows a bottom view of the cover element.
Figure 9:
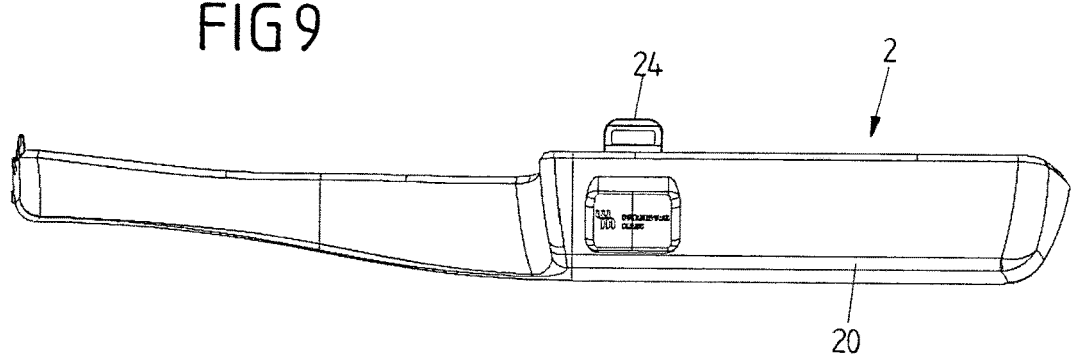
FIG. 9 shows a top view of the cover element.
Figure 10:
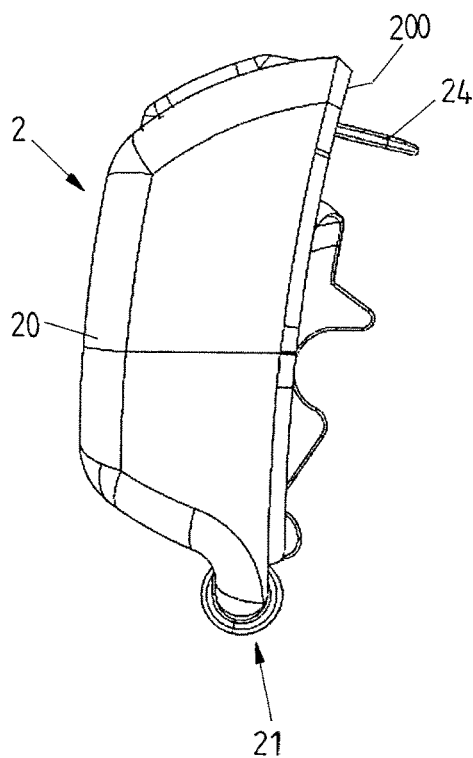
FIG. 10 shows a first side view of the cover element.
Figure 11:
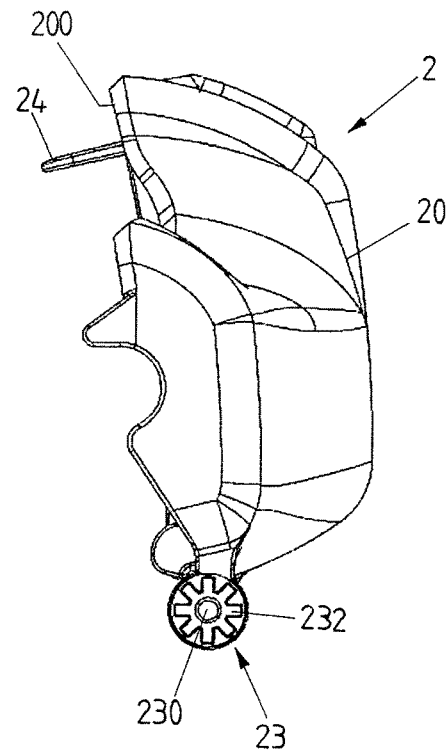
FIG. 11 shows a second side view of the cover element.

The cover element 2, as it is shown in FIG. 4, is detachable from the housing 10 of the medical device 1 by releasing the hinge connection.

Figure 12:
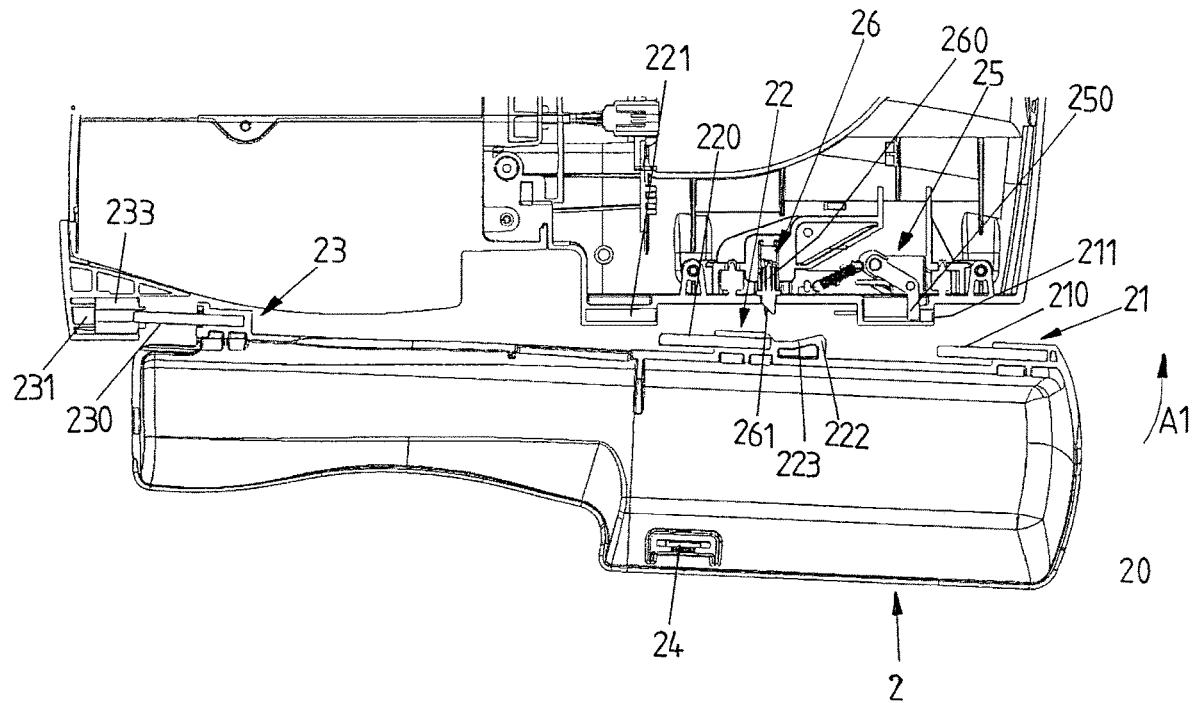
FIG. 12A shows a view of the cover element prior to connection to the housing of the medical device.
FIG. 12B shows a view of the cover element during establishment of the connection.
FIG. 12C shows the cover element in a connected state in which it is connected to the housing.
Figure 12B:
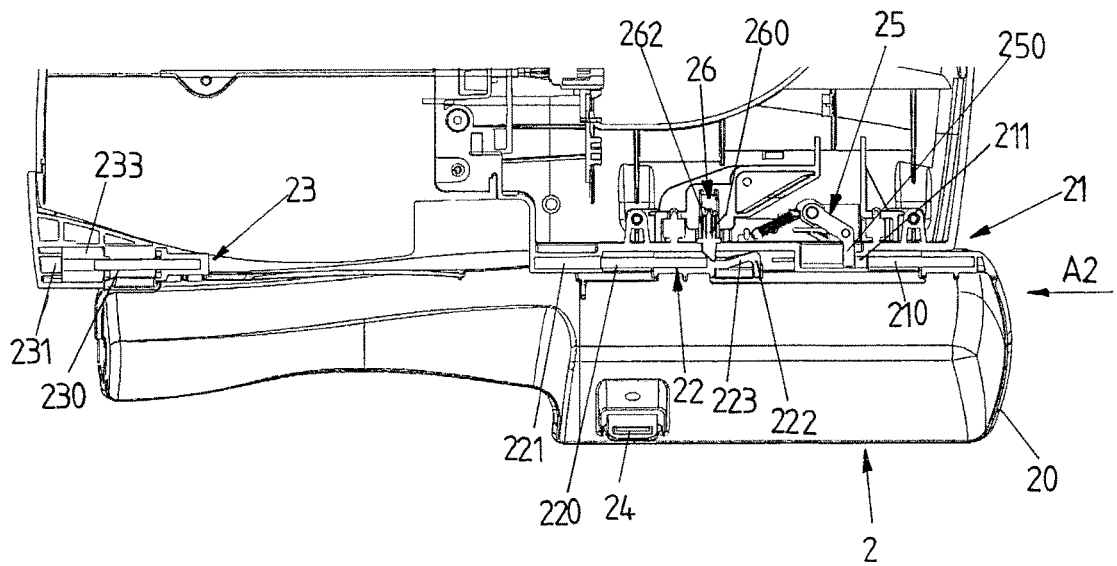
Figure 12C:
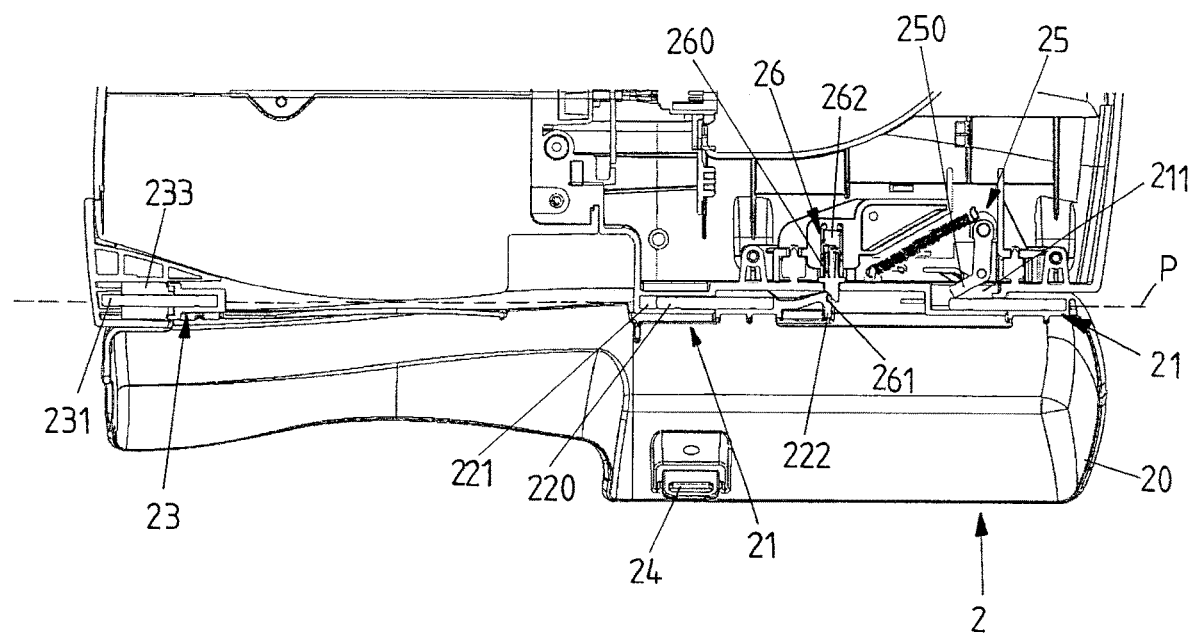

As it is visible from the separate views of FIGS. 5 to 11 of the cover element 2 and from the views of FIG. 12A to 12C showing the cover element 2 during establishment of the connection with the housing 10, each hinge device 21, 22, 23 comprises a hinge pin 210, 220, 230 fixedly arranged on the cover element 2, for example by overmolding a metallic pin element. The hinge pins 210, 220, 230 are, for connecting the cover element 2 to the housing 10 in a pivotable fashion, received in pin receptacles 211, 221, 231 formed on the housing 10 and having the shape of pinholes, the hinge pins 210, 220, 230 in the connected state of the cover element 2 engaging with the pin receptacles 211, 221, 231 as this is visible in FIG. 12C.

As it is indicated for example in FIG. 6, the hinge pin 230 of a first hinge device 23 has a first length L1, which is longer than a second length L2 of the hinge pins 210, 220 of the other two hinge devices 21, 22. This shall facilitate arrangement of the cover element 2 on the housing 10 in that the hinge pin 230 of the first hinge device 23 comes to engage the associated pin receptacle 231 prior to the other pinch pins 210, 220 engaging with their associated pin receptacles 211, 221, as it is visible from FIGS. 12A and 12B.

In particular, for arranging the cover element 2 on the housing 10 for establishing the (pivotable) connection of the cover element 2 to the housing 10 the cover element 2 is approached towards the housing 10 such that the hinge pin 230 of the hinge device 23 comes into engagement with its associated pin receptacle 231, as it is shown in FIG. 12A. By rotating the cover element 2 in a rotational direction A1 towards the housing 10 the hinge pins 210, 220 of the other hinge devices 21, 22 are approached towards their associated pin receptacles 211, 221 to reach the position shown in FIG. 12B, upon which the hinge pins 210, 220, 230 can be brought into full engagement with their associated pin receptacles 211, 221, 231 by laterally moving the cover element 2 in an insertion direction A2 to reach the connected state shown in FIG. 12C.

The connection of the cover element 2 to the housing 10 may be possible (only) in certain pivoting positions of the cover element 2 with respect to the housing 10, for example in a partially opened position.

The hinge device 23 comprises a damping element 233 in the shape of a cylindrical bushing serving to dampen a pivoting movement of the cover element 2 in between its closed position and the opened position. As visible for example from FIGS. 5 and 11, the cover element 2 comprises an engagement face 232 which comes into operative connection with the damping element 233 when connecting the cover element 2 to the housing 10, such that in the connected state the damping element 233 provides for a damping of the rotational movement of the cover element 2 with respect to the housing 10.

The damping element 233 may for example provide for a friction in between the cover element 2 and the housing 10 in order to dampen the pivoting movement. Alternatively, the damping element 233 may comprise a damping fluid such as an oil or the like which provides for a dampening of the pivoting movement.

The hinge device 21 comprises a sensor device 25 having a lever 250 movable within the pin receptacle 211 by interaction with the hinge pin 210 upon insertion into the pin receptacle 211. In particular, when inserting the hinge pin 210 into the pin receptacle 211 by moving the cover element 2 laterally in the insertion direction A2 with respect to the housing 10, the hinge pin 210 acts onto the lever 250 to pivot the lever 250 from a rest position towards a deflected position, the pivoting being detectable by a suitable sensor such that the sensor device 25 may output a sensing signal indicative whether the cover element 2 is in its connected state connected to the housing 10.

The lever 250, in one embodiment, is pretensioned towards the rest position (FIG. 12A, 12B) for example by means of a suitable spring element such that, upon removing the cover element 2 from the housing 10, the lever 250 resumes its initial position.

In the vicinity of the hinge device 22 a blocking device 26 having a blocking pin 260 is arranged. The blocking pin 260 is displaceable with respect to an outer housing face from a normal rest position in a direction transverse to the pivoting axis P and serves to interact with a blocking element 222 in the shape of a protrusion arranged on the cover element 2 next to the hinge pin 220.

The blocking element 222 comprises a run-up slope 223 having a rather small inclination, the run-up slope 223 interacting with the blocking pin 260 for deflecting the blocking pin 260 when laterally moving the cover element 2 with respect to the housing 10 for establishing the engagement of the hinge pins 210, 220, 230 with the pin receptacles 211, 221, 231. Once the engagement has been established and the blocking element 222 has been moved past the blocking pin 260, the blocking pin 260—due to a pretensioning force of a spring element 262—snaps back into place into its normal rest position, as this is visible from FIG. 12C. In this way the blocking pin 260 comes to lie beyond an end of the blocking element 222 opposite to the hinge pin 220, such that the engagement of the hinge pins 210, 220, 230 in the associated pin receptacles 211, 221, 231 is blocked and cannot be released, at least not without releasing the blocking by the blocking pin 260.

The blocking pin 260 comprises a run-up slope 261 having a rather large inclination and acting together with a corresponding slope at the end of the blocking element 222 associated with the blocking pin 260 in the connected state (FIG. 12C). Because of the run-up slope 261 and its interaction with the blocking element 222 on the cover element 2, if the cover element 2 is forced with a sufficient force in a direction opposite to the insertion direction A2, the blocking pin 260 is deflected and pushed into the housing 10 by interaction with the blocking element 222, such that the blocking of the cover element 2 is released and the cover element 2 can be detached from the housing 10 by removing the hinge pins 210, 220, 230 from the pin receptacles 211, 221, 231. The cover element 2 hence can be taken off the housing 10.

The cover element 2 comprises a lock element 24 (see for example FIGS. 8 to 11) which serves to interact with a lock 241 arranged on the housing 10 (see FIG. 1). When closing the cover element 2 the locking element 24 is locked by means of the lock 241, which can be actuated by a key or the like and preferably is biased towards its locked position such that, if not actuated, the lock 241 is in its locked position and hence automatically locks the cover element 2 if the cover element 2 is closed. By actuating the lock 241 the lock element 24 can be unlocked such that the cover element 2 can be opened with respect to the housing 10.

In one embodiment, the medical device 1 comprises a control device 14 (schematically indicated in FIG. 2) serving to control operation of the medical device 1, in particular infusion operations to be carried out by the medical device 1.

For controlling the operation of the medical device 1, the control device 14 may take into account sensor signals of the sensor device 25 as well as of a locking sensor monitoring a lock state of the lock 241.

The control device 14 may in particular be configured to enable an infusion operation if the cover element 2 is removed from the housing 10, dependent potentially upon the medication to be delivered and/or the care area of a hospital in which the medical device 1 is to be used. For example, for some medications and/or care areas an operation with the cover element 2 removed may be admissible. For other medications and/or care areas, in contrast, it may be mandatory to connect the cover element 2 to the housing 10 and to bring the cover element 2 in its closed position.

Additionally or alternatively, the control device 14 may be configured to enable an infusion operation if the cover element 2 is connected to the housing 10, but in that case only if the cover element 2 is in its closed position.

In its closed position, the cover element 2, with an edge 200 at least partially surrounding the body 20 of the cover element 2, is in close abutment with the housing 10 and preferably is received within a corresponding recess of the housing 10, as it is visible for example from FIG. 1. Due to its rounded shape and the close abutment of the edge 200 with the housing 10, an opening of the cover element 2 by means of an external tool is, as far as possible, prevented such that an unauthorized party may and not tamper with the cover element 2 to force its opening.

The idea underlying the invention is not limited to the embodiments described above, but may be implemented in an entirely different fashion in entirely different embodiments.

In particular, the invention in principle also is applicable to medical devices other than syringe infusion devices, for example volumetric (peristaltic) infusion devices having a cover element in the shape of a door.

The cover element may fully close the receptacle or may only partially cover the receptacle in its closed position.

In the illustrated embodiment three hinge devices are used to pivotably connect the cover element to the housing. However, also other numbers of hinge devices are conceivable, in principle one hinge device being sufficient to pivotably connect the cover element to the housing.

LIST OF REFERENCE NUMERALS

1 Medical device
10 Housing
12 Receptacle
120 Pusher device

121 Guide track
122 Clamping device
13 Fixation device (clamp)
14 Control device
2 Cover element
20 Cover body
200 Edge
21 Hinge device
210 Hinge pin
211 Pin receptacle
22 Hinge device
220 Hinge pin
221 Pin receptacle
222 Blocking element
223 Run-up slope
23 Hinge device
230 Hinge pin
231 Pin receptacle
232 Engagement face
233 Damping element
24 Lock element
240 Engagement opening
241 Lock device
25 Sensor device
250 Lever element
26 Blocking device
260 Blocking pin
261 Run-up slope
262 Spring element
3 Pumping apparatus
30 Connector
31 Delivery line
32 Body
33 Piston
330 Piston head
A1, A2 Movement
B Actuation direction
L1, L2 Length
O Opening direction
P Pivot axis

The invention claimed is:

1. A medical device for administering a medical solution to a patient, comprising:
a housing;
a receptacle for receiving a pumping apparatus for administering the medical solution to the patient;
a cover element for covering the receptacle,
wherein the cover element, in a connected state, is pivotably connected via a hinge connection to the housing to pivot about a pivot axis, the hinge connection being releasable for detaching the cover element from the housing; and
a blocking device disposed at the pivot axis, the blocking device for blocking, in the connected state of the cover element, movement of the cover element directed along the pivot axis with respect to the housing to detach the cover element from the housing,
wherein the blocking device comprises a blocking pin displaceably arranged on one of the housing and the cover element transverse to the pivot axis, the blocking pin being configured to interact with a blocking element arranged on the other of the housing and the cover element for blocking a movement of the cover element with respect to the housing opposite to an insertion direction directed along the pivot axis.

2. The medical device according to claim 1, wherein the hinge connection is formed by at least one hinge device configured to pivotably connect the cover element to the housing.

3. The medical device according to claim 2, wherein the at least one hinge device comprises a hinge pin arranged on one of the cover element and the housing and a pin receptacle arranged on the other of the cover element and the housing, the pin receptacle being configured to pivotably receive the hinge pin.

4. The medical device according to claim 3, wherein the hinge pin is insertable into the pin receptacle in the insertion direction directed along the pivot axis for establishing the hinge connection.

5. The medical device according to claim 4, wherein a first hinge device of the hinge connection comprises a first hinge pin, and a second hinge device of the hinge connection comprises a second hinge pin, wherein the first hinge pin and the second hinge pin are configured such that, when connecting the cover element to the housing, the first hinge pin of the first hinge device comes into engagement with an associated first pin receptacle prior to the second hinge pin of the second hinge device coming into engagement with an associated second pin receptacle.

6. The medical device according to claim 3, further comprising a sensor device for detecting whether the hinge pin is received in the pin receptacle.

7. The medical device according to claim 6, wherein the sensor device comprises a movable lever configured to interact with the hinge pin when inserting the hinge pin into the pin receptacle.

8. The medical device according to claim 2, wherein the at least one hinge device comprises a damping element for damping a pivoting movement of the cover element with respect to the housing.

9. The medical device according to claim 1, wherein the blocking pin and/or the blocking element comprise a run-up slope configured to cause a displacement of the blocking pin for enabling the connecting of the cover element to the housing and/or the releasing of the cover element from the housing.

10. The medical device according to claim 1, wherein the cover element comprises a lock element for locking the cover element with the housing when the cover element is connected to the housing and is closed for covering the receptacle.

11. The medical device according to claim 1, wherein the cover element comprises a cover body formed from a transparent material.

12. The medical device according to claim 1, further comprising a control device constituted to evaluate whether the cover element is connected to the housing and is closed for covering the receptacle in order to enable an administration operation dependent on the evaluation.

13. A medical device for administering a medical solution to a patient, comprising:
a housing;
a receptacle for receiving a pumping apparatus for administering the medical solution to the patient;
a cover element for covering the receptacle,
the cover element, in a connected state, being pivotably connected to the housing about a pivot axis by means of a hinge connection, the hinge connection being releasable for detaching the cover element from the housing, the hinge connection being formed by at least one hinge device configured to pivotably connect the cover element to the housing, the at least one hinge device comprising a hinge pin arranged on one of the cover element and the housing and a pin receptacle arranged on the other of the cover element and the housing, the pin receptacle being configured to pivotably receive the hinge pin, and a sensor device for detecting whether the hinge pin is received in the pin receptacle.

14. The medical device according to claim 13, wherein the sensor device comprises a movable lever configured to interact with the hinge pin when inserting the hinge pin into the pin receptacle.

* * * * *